United States Patent [19]

Nishimura et al.

[11] 4,234,460
[45] Nov. 18, 1980

[54] ADSORBENT FOR ETHYLENE AND PROCESS FOR PREPARATION THEREOF

[75] Inventors: Yasushi Nishimura, Tokyo; Yasuo Uehara, Iruma; Tamio Haga, Iwaki, all of Japan

[73] Assignee: Kureha Kagaku Kogyo Kabushiki Kaisha, Japan

[21] Appl. No.: 941,681

[22] Filed: Sep. 12, 1978

[30] Foreign Application Priority Data

Sep. 22, 1977 [JP] Japan ................................ 52-114057

[51] Int. Cl.³ ...................... B01J 21/18; B01J 23/70; B01D 53/04
[52] U.S. Cl. ................................... 252/447; 423/245; 426/124; 426/419
[58] Field of Search .............................. 252/447, 444; 423/245 R, 245 S; 260/683.15 R; 585/510, 531; 426/124, 419

[56] References Cited

U.S. PATENT DOCUMENTS

| 2,692,295 | 10/1954 | Peters | 252/447 |
| 3,333,017 | 7/1967 | Schuck et al. | 260/683.15 R |

FOREIGN PATENT DOCUMENTS 1091094  11/1967  United Kingdom .................... 252/413

OTHER PUBLICATIONS

Australian J. Exp. Agr. Animal Husb.-vol. 10 (1970), pp. 237-240, Scott, K. J. et al.

Primary Examiner—P. E. Konopka
Attorney, Agent, or Firm—Stevens, Davis, Miller & Mosher

[57] ABSTRACT

A novel adsorbent for ethylene prepared by contacting an active carbon with at least one metal substance selected from the group consisting of copper, iron, cobalt, nickel, and their salts in the presence of nitric acid; heating the same at a temperature of 150° to 900° C. in an atmosphere of inert gas and thereby to obtain the adsorbent containing 0.01 to 20% by weight of said metal(s) therein.

7 Claims, No Drawings

ADSORBENT FOR ETHYLENE AND PROCESS FOR PREPARATION THEREOF

The present invention relates to a novel adsorbent for ethylene and to a process for the preparation of the adsorbent.

Ethylene is used in large amounts as an industrial raw material. For example, it is used as a starting material for the manufacture of various chemical products such as polyethylene, ethylene-propylene rubber, vinyl chloride, styrene, ethylene chloride and acetaldehyde. Otherwise, it is converted into ethylene oxide and, the latter is used as a raw material for the synthesis of various products. Ethylene is also used as a maturing agent for fruits. Although ethylene is held to possess little toxicity, it is nevertheless undesirable for gaseous ethylene to be released into the ambient atmosphere because ethylene lowers the oxygen concentration in the air and consequently brings about hypoxia and, above all, it possesses in itself an anesthetizing activity. Further, ethylene is known as one of the maturation hormones for plants and is used for accelerating the maturation of fruits. In this case, there ensues a chain reaction that fruits in the course of maturation generate ethylene in themselves and this ethylene promotes the maturation of the fruits. If the ethylene thus generated by fruits is effectively removed, it will become possible to control the self-maturation of fruits and consequently to elongate the storage period of the fruits.

Generally, active carbon is effective to some extent in removing atmospheric ethylene. The adsorbing capability of active carbon, however, is extremely small to hydrocarbons having small numbers of carbon atoms such as ethylene. Characteristically, the adsorbing capacity of active carbon depends on the concentration of the gas present, i.e. it decreases with the decreasing concentration of the gas. This trend (dependency of the adsorbing capability upon the gas concentration) is particularly conspicuous when active carbon is used on hydrocarbons which have small numbers of carbon atoms such as ethylene. Consequently, active carbon must be used in a large amount for the removal of ethylene which is present in a low concentration. In most cases, a sufficient decrease in the ethylene concentration is not easily obtained by increasing the amount of active carbon in such a treatment. In some cases involving the removal of ethylene, some other components are desired to be removed simultaneously with ethylene. In this respect, an adsorbent of the type which manifests an advantageous adsorbing capacity on hydrocarbons having large numbers of carbon atoms and on gaseous components possessing relatively high boiling points and also excels in ability to adsorb ethylene proves to be most desirable. Practical utility of such an adsorbent will be great.

A principal object of the present invention, therefore, is to provide a novel adsorbent of which the adsorbing capability for ethylene is excellent even when the ethylene is present in a low concentration. It has now been found that an excellent adsorbent for ethylene is obtained by bringing an active carbon into contact with at least one metal selected from the group consisting of copper, iron, cobalt and nickel or one compound of those metals under a condition acidified with nitric acid and thereby allowing the active carbon to contain therein the metal in an amount of from 0.01 to 20% by weight, and subsequently heating the resultant metal-containing active carbon in an inert atmosphere at a temperature in the range of from 150° to 900° C.

The adsorbent for ethylene of the present invention obtained as described above manifests, in the desired removal of ethylene, an excellent ability never attainable with a conventional active carbon. It can be effectively applied to the uses which require removal of ethylene. The above-mentioned adsorbent also possesses the ability expected of a conventional active carbon and is capable of removing other gaseous components. Now, the adsorbent of the present invention will be described in detail herein below.

As to the kind of active carbon to be used herein, the active carbon spheres of high strength produced from pitch as are disclosed by Japanese Patent Publication No. 76/1976 prove to be most desirable in terms of handling at the time of use. Otherwise, molded carbon, crushed carbon and powdered carbon which are derived from coconut shells and other ligneous materials and coal may be used. That is, the raw material for the adsorbent is not specifically limited.

As to the kind of metal to be used herein, copper, iron, cobalt and nickel are effective. They may be used either singly or in combination of two or more members. The amount of the metal to be incorporated in the active carbon is in the range of from 0.01 to 20% by weight, preferably from 0.1 to 10% by weight, based on the active carbon.

If the metal content is smaller, the satisfactory effect to be brought about by the addition of the metal is not obtained. If the metal content is larger, however, the effect expected is not increased proportionally to the amount added therein and, consequently, the efficiency of the incorporated metal is impaired and the adsorbing capability of the active carbon on other gaseous components is accordingly deteriorated.

Generally, the incorporation of the above-mentioned metal into the active carbon is accomplished most conveniently by allowing an aqueous solution of a salt of the metal to be absorbed by the active carbon. For this purpose, the active carbon may be dispersed in a large volume of an aqueous solution of the metal salt and, upon completion of the adsorption of the metal salt, separated from the solution by filtration. Or else, for convenience and simplicity, the active carbon and the aqueous solution of the metal salt may be mixed in proper amounts such that substantially all the aqueous solution will be absorbed by the active carbon. Alternatively, an active carbon which has incorporated the metal in advance may be used as the raw material.

As described above, the incorporation of the metal into the active carbon can be effected by using any of the known methods. No matter which method may be adopted for the purpose of this incorporation, it is an essential prerequisite that the contact of the metal with the active carbon should take place under a condition acidified by nitric acid. No advantageous effect on the adsorbing capability can be obtained either by using a neutral or alkaline salt of the metal alone or by using a salt of any organic acid such as an acetate alone. Even when such a salt is used, the effect aimed at by the present invention can be obtained by adding nitric acid to the system and thereby acidifying it. In cases where an active carbon containing the metal is used, the desired effect can be obtained by impregnating the active carbon with nitric acid. For the purpose of acidification, nitric acid at a concentration from 0.1 to less then 5N can be used. Using of nitric acid of a concentration exceeding 5N, however, is undesirable because the nitric acid is decomposed by the active carbon. Generally, the allowable concentration of nitric acid for the acidification is in the range of from ½ to 2N.

A salience of the present invention resides in the fact that the process involves a step of bringing the active carbon into contact with the metal under a condition acidified with nitric acid.

The adsorbent aimed at by the present invention is obtained by drying the active carbon which has incorporated the metal as described above and subsequently heating the dried active carbon in an inert atmosphere. The expression "inert atmosphere" as used herein means an atmosphere which does not substantially react with the carbon and the metal at the temperatures at which the above-mentioned heating is carried out. Helium, argon, nitrogen, etc. can be used at a temperature in a larger range. At temperatures not exceeding 700° C., steam or hydrogen may be used for that purpose. The temperature at which the heating is carried out is in the range of from 150° to 900° C., preferably from 200° to 700° C. The heating carried out at a temperature below 150° C. fails to give the desired effect on the product sufficiently. If it is carried out at a temperature exceeding 900° C., the effect is lost because the metal is sintered onto the carbon. The duration of this heating is generally in the range of from 0.1 hour to several hours.

The active carbon which is obtained under the conditions specified by the present invention as described above functions excellently in the adsorption of ethylene even at its low concentration. The cause of this excellent capability has not yet been elucidated but may be considered that active centers are formed on/in the active carbon, which are advantageous for the adsorption of ethylene under the particular conditions specified by the present invention.

Now, working examples of the present invention will be cited herein below to illustrate the effect of the present invention, however, none of them is intended to limit the scope of the present invention.

EXAMPLES 1-14 AND COMPARATIVE EXAMPLES 1-8

With 100 ml of an aqueous solution of a variety of metal salt, which had, or had not, been acidified with nitric acid (to ½-N), 100 g of a varying kind of granular active carbon (carbon spheres prepared from pitch, crushed carbon from coconut shells or crushed carbon from coal) were throughly mixed until the solution was thoroughly absorbed by the active carbon. Then, the salt-impregnated active carbon was dried at a temperature of from 110° to 120° C., heated in a quartz glass tube under a flow of nitrogen or steam at a varying temperature for one hour by means of a tubular electric furnace, then cooled to room temperature and withdrawn from the tube to be used as a test specimen. In cases where even steam was used for heating the active carbon, the heating to a temperature up to 200° C. was carried out by using a flow of nitrogen.

A test specimen of the thus prepared adsorbent (5 g) was then placed in a glass container having an inner volume of 1.1 liters and after having gaseous ethylene sealed therein at a concentration of 100 ppm by volume, the time change of the concentration of gaseous ethylene in the container was traced by a gas chromatograph provided with a hydrogen flame detector. The conditions for the preparation of each test specimen and the results of the removal of gaseous ethylene were shown in Tables 1 and 2. The rate of removal of gaseous ethylene is represented by the following formula:

$$\left(1 - \frac{\text{conc. of ethylene in the treated gas}}{\text{conc. of ethylene in the initial gas}}\right) \times 100 = \text{rate of}$$

removal of gaseous ethylene (%) conc.=ppm by volume.

TABLE 1

| | Conditions for preparation of the absorbent | | | | | Rate of removal of ethylene | | | | |
|---|---|---|---|---|---|---|---|---|---|---|
| | Origin of active | | Metal/active carbon | Heating tempera- | Heating | Period of contact with the gas and the adsorbent (min) | | | | |
| Example | carbon | Metal salt | (% by weight) | ture (° C.) | atmosphere | 1 | 5 | 10 | 20 | 30 |
| 1 | Pitch | Copper nitrate | 1 | 400 | nitrogen | 85 | 98 | 100 | 100 | 100 |
| 2 | Pitch | Iron nitrate | 1 | 500 | nitrogen | 77 | 90 | 96 | 100 | 100 |
| 3 | Pitch | Cobalt nitrate | 1 | 500 | nitrogen | 70 | 89 | 95 | 100 | 100 |
| 4 | Pitch | Nickel nitrate | 2 | 700 | nitrogen | 71 | 93 | 98 | 100 | 100 |
| 5 | Pitch | Copper acetate | 2 | 500 | nitrogen | 75 | 90 | 98 | 100 | 100 |
| 6 | Pitch | Copper nitrate | 0.05 | 600 | nitrogen | 70 | 90 | 95 | 98 | 100 |
| 7 | Pitch | Copper nitrate | 0.5 | 200 | nitrogen | 73 | 95 | 99 | 100 | 100 |
| 8 | Pitch | Copper nitrate | 5 | 500 | steam | 80 | 98 | 100 | 100 | 100 |
| 9 | Pitch | Copper nitrate | 10 | 500 | nitrogen | 82 | 99 | 100 | 100 | 100 |
| 10 | Pitch | Basic coper acetate | 3 | 500 | steam | 72 | 96 | 98 | 100 | 100 |
| 11 | Pitch | Copper nitrate + iron nitrate | 0.5 + 1.0 | 600 | nitrogen | 80 | 96 | 100 | 100 | 100 |
| 12 | Pitch | Copper sulfate | 2 | 200 | nitrogen | 81 | 97 | 100 | 100 | 100 |
| 13 | Coconut shells | Copper sulfate | 1 | 600 | nitrogen | 70 | 97 | 100 | 100 | 100 |
| 14 | Coal | Copper sulfate | 1 | 600 | nitrogen | 70 | 98 | 100 | 100 | 100 |

Note:
Source of the acidity was nitric acid in all examples.

TABLE 2

| Comparative Example | Origin of active carbon | Metal salt | Metal/active carbon (% by weight) | Source of acidity | Heating temperature (°C.) | Heating atmosphere | Rate of removal of ethylene — Period of contact with the gas and the adsorbent (min) | | | | |
| --- | --- | --- | --- | --- | --- | --- | --- | --- | --- | --- | --- |
| | | | | | | | 1 | 5 | 10 | 20 | 30 |
| 1 | pitch | none | 0 | none | not heated | — | 58 | 77 | 80 | 81 | 81 |
| 2 | cocconut shells | none | 0 | none | not heated | — | 57 | 75 | 79 | 80 | 80 |
| 3 | coal | none | 0 | none | not heated | — | 55 | 70 | 75 | 78 | 77 |
| 4 | pitch | Copper acetate | 2 | acetic acid | 500 | nitrogen | 65 | 83 | 85 | 85 | 85 |
| 5 | pitch | Nickel acetate | 1 | acetic acid | 500 | nitrogen | 64 | 81 | 86 | 86 | 86 |
| 6 | pitch | Silver nitrate | 0.5 | nitric acid | 700 | nitrogen | 67 | 84 | 85 | 85 | 85 |
| 7 | pitch | Zinc nitrate | 3 | nitric acid | 500 | nitrogen | 48 | 69 | 80 | 80 | 80 |
| 8 | Commercially available active carbon carrying palladium | | 5 | none | not heated | — | 27 | 30 | 30 | 30 | 30 |

The removal of gaseous ethylene in the container substantially reached an equilibrium after ten minutes' standing of the gaseous ethylene with the test specimen. All the adsorbents prepared in accordance with the process of the present invention provided complete removal of gaseous ethylene, thus demonstrating their excellent capability as shown in Table 1.

In contrast, conventional active carbons and the products prepared not in accordance with the process of the present invention provided slow removal of gaseous ethylene and failed to lower the residual ethylene concentrations below the levels of 15 to 20 ppm, indicating the rate of removal of gaseous ethylene only in the range of from 80 to 85% as shown in Table 2.

EXAMPLE 15

A test specimen prepared in Comparative Example 4 having a low capability for removal of gaseous ethylene was allowed to absorb water acidified with nitric acid (1N), left to stand at room temperature for one hour, then dried at a temperature of 110° to 120° C. and subsequently heated under the flow of nitrogen and 500° C. for one hour. The specimen thus produced removed gaseous ethylene as shown in Table 3.

TABLE 3

| Time period of contact of ethylene and the specimen (minutes) | 1 | 5 | 10 | 20 | 30 |
| --- | --- | --- | --- | --- | --- |
| Rate of removal of gaseous ethylen (%) | 84 | 98 | 100 | 100 | 100 |

EXAMPLE 16

To 95 g of an aqueous solution of copper nitrate acidified with nitric acid (½N) and containing 3 g of copper as the nitrate, 100 g of active carbon spheres prepared from pitch were mixed. The mixture was dried at a temperature of 110° to 120° C. and then heated in a quartz glass tube under a flow of nitrogen by means of a tubular electric furnace up to 250° C. At this point, the flow of nitrogen was switched to that of steam and the mixture was heated up to 550° C., at which temperature it was kept for one hour. The heated mixture was subsequently cooled to 200° C. and, with the flow of steam again switched to that of nitrogen, cooled to room temperature to obtain a test specimen.

A varying weight (in the range of from 0.5 to 5 g) of this test specimen was placed in a glass container having an inner volume of 1.1 liters and having gaseous ethylene sealed therein in a concentration of 500 ppm, and it was left to stand in the container for more than 30 minutes until a sufficient equilibrium was reached. Then, the atmosphere within the container was tested for gaseous ethylene concentration by a gas chromatograph provided with a hydrogen flame detector. The relation between the gas concentration at the equilibrium and the removal of gaseous ethylene per unit weight of the active carbon (curve of adsorption isotherm) was obtained. The same test specimen was also used to perform a similar test on ethane and obtain a curve of adsorption isotherm for ethane.

Entirely the same test was further performed on a product prepared from pitch. The results were shown in Table 4.

The removal of gaseous ethylene per weight of the test specimen was conspicuously high in the case of the adsorbent prepared in accordance with the process of this invention.

The amount of ethane adsorbed by the adsorbent of this invention was equal to that obtained by a not-treated active carbon, indicating that the ability of activated carbon for the removal of ethane was not impaired by the treatment given in accordance with the process of the present invention.

TABLE 4

| | Concentration at equilibrium (ppm) | Active carbon according to the present invention | | not-treated active carbon | |
| --- | --- | --- | --- | --- | --- |
| | | Ethylene | Ethane | Ethylene | Ethane |
| Amount of adsorb (cc/100 g of active carbon) | 300 | 95 | 35 | 20 | 33 |
| | 100 | 63 | 12 | 7.4 | 12 |
| | 30 | 40 | 4.6 | 2.5 | 4.4 |

What is claimed is:

1. An adsorbent for removing ethylene from a gas containing ethylene, said adsorbent containing active carbon and from 0.01 to 20% by weight of copper, said adsorbent having been obtained by
   (a) contacting an active carbon with copper or a salt thereof in the presence of nitric acid;

(b) heating the resultant mixture at a temperature of 150° to 900° C. in an inert gas atmosphere whereby the desired adsorbent is obtained.

2. An adsorbent of claim 1, wherein step (a) is carried out by adding said active carbon into an aqueous nitric acid solution of a salt of said copper.

3. An adsorbent of claim 2, wherein the concentration of nitric acid is from 0.1 N to 5 N.

4. An adsorbent of claim 1, wherein said active carbon is premixed with said copper or salt thereof and then added into an aqueous nitric acid solution.

5. An adsorbent of claim 4, wherein the concentration of nitric acid is from 0.1 N to 5 N.

6. An adsorbent of claim 1, 2, 3, 4 or 5, wherein said temperature is 200° to 700° C.

7. An adsorbent of claim 1, 2, 3, 4 or 5, wherein said adsorbent contains said copper in an amount of from 0.1 to 10% by weight.

* * * * *